United States Patent [19]

Commarmot

[11] Patent Number: 4,805,469
[45] Date of Patent: Feb. 21, 1989

[54] APPARATUS FOR AUTOMATICALLY TAKING AND ANALYZING SAMPLES OF SUBSTANCES WHICH ARE MADE AVAILABLE IN RANDOM MANNER

[75] Inventor: Roger Commarmot, Lyons, France

[73] Assignee: Rhone-Poulenc Recherches, Courbevoie, France

[21] Appl. No.: 63,092

[22] Filed: Jun. 17, 1987

[30] Foreign Application Priority Data

Jun. 17, 1986 [FR] France ................ 86 08990

[51] Int. Cl.⁴ ............................................ G01N 35/00
[52] U.S. Cl. .................................... 73/864.81; 422/64
[58] Field of Search ............ 73/864.81, 864.85, 864.86, 73/864.87, 864,01, 864.11, 864.12, 864.21, 864.22, 864.23, 864.24, 864.25, 863.01; 422/63, 64, 69, 70, 81

[56] References Cited

U.S. PATENT DOCUMENTS

| 3,764,268 | 10/1973 | Kosowsky et al. | 422/64 |
| 3,909,203 | 9/1975 | Young et al. | 422/67 |
| 3,912,456 | 10/1975 | Young | 73/864.22 |
| 3,925,207 | 12/1975 | Scriba | |
| 3,943,766 | 3/1976 | Delany | 374/111 |
| 4,113,436 | 9/1978 | Werder et al. | |
| 4,478,095 | 10/1984 | Bradley et al. | 73/864.21 |
| 4,678,752 | 7/1987 | Thorne et al. | 422/65 |

FOREIGN PATENT DOCUMENTS

| 083474 | 7/1983 | European Pat. Off. | |
| 2542674 | 3/1977 | Fed. Rep. of Germany | |
| 2261516 | 9/1975 | France | |
| 2268267 | 11/1975 | France | |
| 8302160 | 6/1983 | World Int. Prop. O. | 422/70 |

OTHER PUBLICATIONS

Patents Abstracts of Japan, vol. 7, No. 188 (p. 217) Japan-A-58 88 663, Aug. 17, 1983 (Tokyo Shibaura Denki K.K.).

Primary Examiner—Stewart J. Levy
Assistant Examiner—Robert R. Raevis
Attorney, Agent, or Firm—Burns, Doane, Swecker & Mathis

[57] ABSTRACT

Apparatus for automatically taking and analyzing samples of substances made available in random manner, is of the type comprising an analysis assembly including at least two analysis stations having different characteristics, and a module delimiting temporary storage slots for receptacles containing different substances to be analyzed by different methods applicable to each of said substances, said apparatus comprising: receptacles each bearing a code identifying the substance contained therein, the analysis treatment to which is is to be subjected, and a treatment priority attributed thereto; means for detecting the in-use or available status of each analysis station; means for scanning the slots in the storage module for reading the codes of the receptacles and for storing them in priority order in conjuction with the characteristics of the corresponding treatment and the addresses of the slots; means for seeking in priority order correspondence between the treatments to be performed and a currently available compatible analysis station; means for displacing an insertion system into relationship with the available analysis station; means for bringing the selected sample receptacle into relationship with an extraction station; means for extracting at least a portion of the sample from the selected receptacle and for transferring it into the insertion system; means for inserting the sample into the analysis station; means for controlling the operating conditions of the analysis station as a function of the analysis treatment to be performed; and means for returning the insertion system to its home position in readiness for a new operating cycle.

10 Claims, 3 Drawing Sheets

4,805,469

APPARATUS FOR AUTOMATICALLY TAKING AND ANALYZING SAMPLES OF SUBSTANCES WHICH ARE MADE AVAILABLE IN RANDOM MANNER

BACKGROUND OF THE INVENTION

The present invention relates to analyzing samples of substances taken from an industrial fabrication process.

In order to check that a process is running properly, it is common practice to take samples at regular intervals of a product in the course of fabrication, and to analyze the samples by some suitable method: for example by chromatography, in particular gas chromatography; by colorimetry; or by measuring electrical conductivity. It is possible with these methods to analyze the presence of various components in the product and also to determine their relative concentrations. A knowledge of these facts can be used to control the running of an industrial process so as to continuously adjust its operating conditions with a high degree of accuracy as a function of reaction progress and in such a manner as to obtain a finished product whose characteristics are constant or are subject to little variation.

In the past, such analysis methods have required each sample to be individually analyzed by qualified operators, each making use of one or more independently operating analysis stations.

It will readily be understood that this method of proceeding, although capable in some cases of obtaining analysis results which are at least useable even if not particularly reliable or accurate, is unwieldly and expensive when a continuous industrial process is being run, in particular because of the relatively slow response time inherent to this method of analysis.

In order to remedy this drawback, proposals have been made to provide an installation comprising an analysis assembly having a plurality of analysis stations of determined characteristics (e.g. various chromatographs), with the analysis stations receiving substance for analysis from a device for transferring samples which arrive in a predetermined order as a function of the particular stations for which they are intended.

Although such an installation provides a certain saving in time, it is still not entirely satisfactory by virtue of the need to pre-program the operation of the assembly, and consequently of the need to perform an initial sorting operation on the samples, placing them in ordered storage slots as a function of the predetermined availability of the analysis stations and in accordance with a correspondence table.

In this type of installation, sample substance for analysis is taken from storage station. The sample taken is then transferred and injected into the appropriate analysis station. This transfer operation frequently allows the substance to evaporate partially, and as a result the analysis does not accurately reflect the sample as originally taken from the industrial process.

One proposal for improving this situation has been to label each flask containing a sample of product with an identification code that can be read and used to cause an analysis station to perform the appropriate analysis process.

This proposal has the advantage of providing a solution which is closer to the needs of industry which, in modern industrial fabrication processes, are typified by the requirement for rapid, automatic and reliable processing of all types of sample using a process for each sample which is appropriate thereto and regardless of the order in which samples are presented.

However, this proposal is still not entirely satisfactory since it does not take account of a possible priority order attributed to the samples to be processed when, for understandable reasons of speed, capacity, reliability, and/or cost, the analysis installation being used is common to a plurality of fabrication processes taking place simultaneously, which processes therefore provide collections of samples that arrive in random manner but that are to be analyzed according to specific methods and while satisfying relative priorities which may vary.

Preferred implementations of the present invention seek to meet the above requirements by proposing a novel method and novel apparatus for automatically taking and analyzing samples under present day industrial conditions.

SUMMARY OF THE INVENTION

The present invention provides apparatus for automatically taking and analyzing samples of substances made available in random manner, the apparatus being of the type comprising an analysis assembly including at least two analysis stations having different characteristics, and a module delimiting temporary storage slots for receptacles containing different substances to be analyzed by different methods applicable to each of said substances, said apparatus comprising:

receptacles each bearing a code identifying the substance contained therein, the analysis treatment to which it is to be subjected, and a treatment priority attributed thereto;

means for detecting the in-use or available status of each analysis station;

means for scanning the slots in the storage module for reading the codes of the receptacles and for storing them in priority order in conjunction with the characteristics of the corresponding treatment and the addresses of the slots;

means for seeking in priority order correspondence between the treatments to be performed and a currently available compatible analysis station;

means for displacing an insertion system into relationship with the available analysis station;

means for bringing the selected sample receptacle into relationship with an extraction station;

means for extracting at least a portion of the sample from the selected receptacle and for transferring it into the insertion system;

means for inserting the sample into the analysis station;

means for controlling the operating conditions of the analysis station as a function of the analysis treatment to be performed; and means for returning the insertion system to its home position in readiness for a new operating cycle.

BRIEF DESCRIPTION OF THE DRAWINGS

An embodiment of the invention is described by way of example with reference to the accompanying drawings, in which.

DETAILED DESCRIPTION OF A PREFERRED EMBODIMENT OF THE INVENTION

Figure 1:
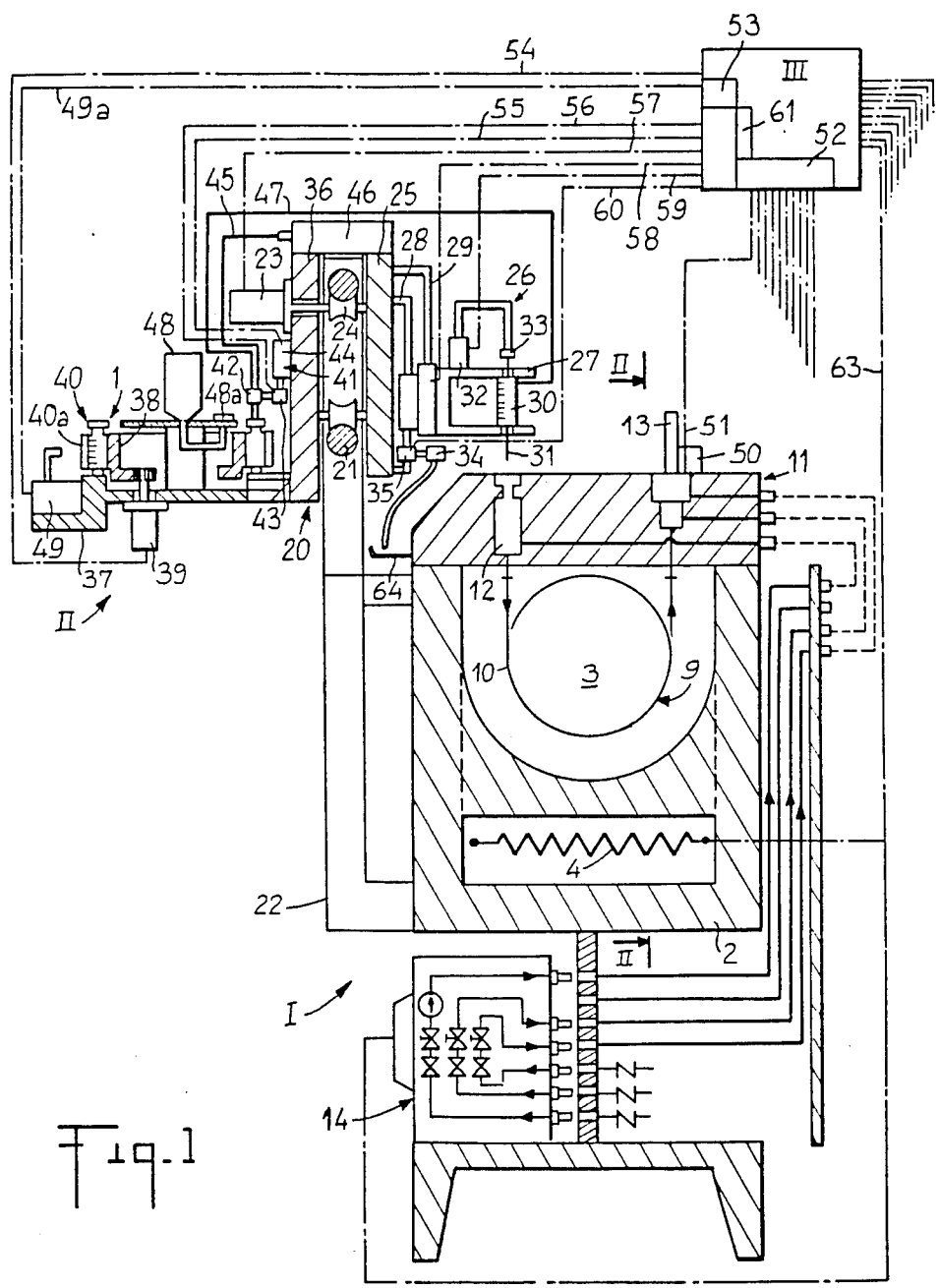
FIG. 1 is a cross-section through apparatus in accordance with the invention.
Figure 2:
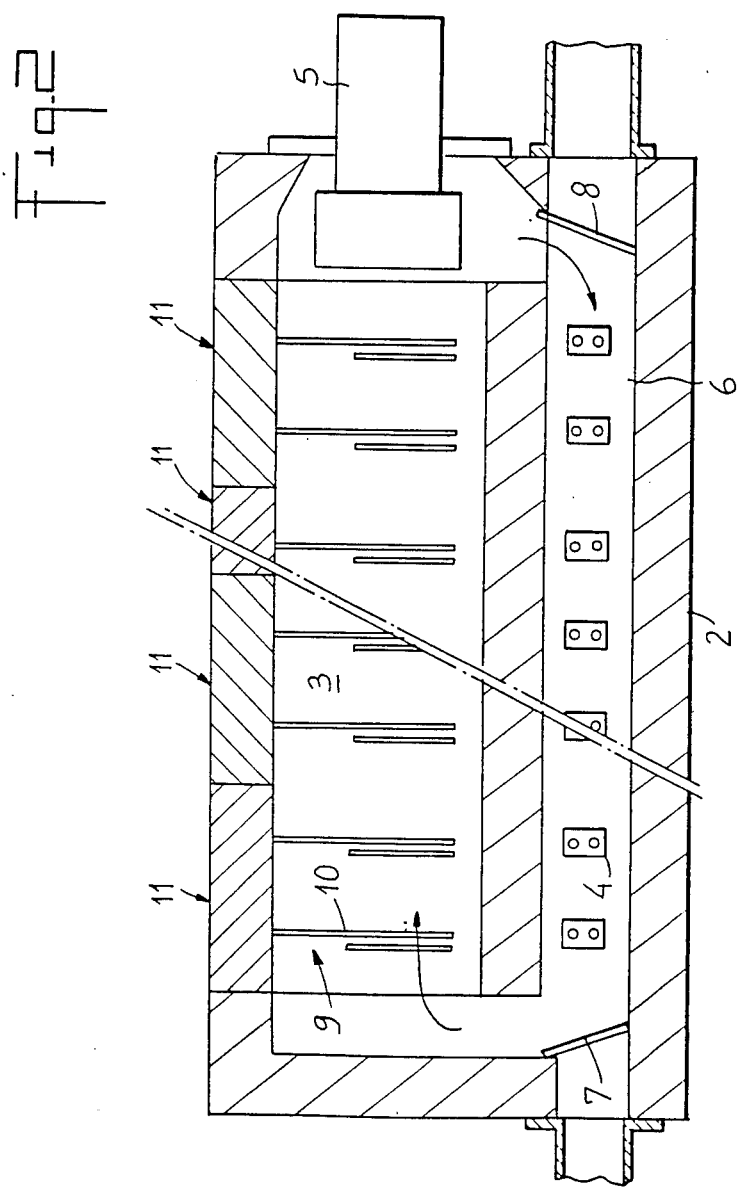
FIG. 2 is a fragmentary elevation section taken on line II—II of FIG. 1.

FIGS. 1 and 2 are sections through apparatus in accordance with the invention.

The apparatus operates automatically to analyze samples of substances contained in receptacles or flasks 1 which arrive as random succession and which are hermetically sealed by a septum (i.e. a membrane suitable for being pierced by the needle of a syringe). To this end, the apparatus comprises an analysis assembly I which is associated with an assembly II for temporarily storing and for transferring samples, with these two assemblies being controlled to operate together by means of calcuting machinery III which takes account of various parameters described below.

The analysis assembly I may be of any appropriate type depending on the specific analysis method to be applied to each of the sample substances. Appropriate devices include the following: colorimeters; gas and/or liquid chromatography devices; and means for measuring electrical conductivity. In the following description and in the drawings, specific mention is made, by way of example, solely of a method based on gas chromatography.

The analysis assembly I includes an oven 2 delimiting at least one heating enclosure 3 asociated with heater means 4 for raising its temperature and with circulation means 5 for setting up a flow of a heat-conveying fluid. The oven 2 may be made in numerous different ways, and in the example shown it is constituted by a heating enclosure 3 having a horizontal axis and having its ends put into communication with a recycling circuit 6 which includes the heater means 4 and the circulation means 5. The heater means 4 may be constituted by a battery of electrical resistance elements, and the circulation means 5 may be constituted by a centrifugal motor-driven blower suitable for circulating air, for example in the direction of the arrows, which air is taken from the surroundings via an inlet valve 7 suitable for being closed manually or automatically, and optionally coupled with a discharge valve 8.

The enclosure 3 is intended to contain the active components of n analysis stations 9 constituted in this particular case by chromatographs having different operating and analysis characteristics. The chromatographs 9 may be fitted in any appropriate manner to the oven 2 so that their separation columns 10 are fully contained within the enclosure 3. In a particularly appropriate disposition, the chromatographs 9 may be grouped into modules such as 11, with two chromatographs per module, for example, thereby enabling the assembly to be rapidly altered when the analysis characteristics of the stations in operation need to be modified as a function of the substances to be analyzed.

Regardless of the particular constructional characteristics used, the various analysis stations 9 are disposed so that their injectors 12 and their detection means 13 are aligned while also being accessible from a single common face of the oven 2. FIG. 2 shows that the assembly may include at least four chromatograph modules, however it is clear that this number is not limiting and that the analysis assembly may be adapted to include some other number of modules depending on the intended applications.

For each analysis station 9, the assembly I includes a control module 14 constituted by the various necessary accessories, in particular valves and regulators for adjusting the flowrates of the vector gas, the fuel, and the oxidizer.

The analysis assembly I is associated with the assembly II which mainly comprises a carriage 20 mounted on a support and guide path 21 which is fixed on a structure 22 located above one side of the assembly I. The guide path 21 extends parallel to the line of injectors 12 and in the example shown it is situated to one side of the assembly I and not directly over it. Naturally other constructional dispositions could be devised.

The carriage 20 includes a drive member 23 such as motor for rotating a pinion or the like 24 which co-operates with a complementary component of the path 21.

The carriage 20 has a first fixing plate 25 which is substantially vertical and which carries a motorized insertion head 26 for inserting at least a portion of a sample into an analysis station 9. In the example show, this is an injector head including a clamp 27 which is movably mounted on a vertical support slide 28 by means of a double-acting linear actuator or jack 29. The clamp 27 is intended to hold an injection syringe 30 between its jaws, with the needle 31 of the syringe being displaceable by means of the carriage 20 along a path vertically above the line of injectors 12. The supporting clamp 27 also serves to hold a motor 32 of the double-acting linear type, i.e. capable of acting positively in both directions, in contact with the moving member 33 of the syringe 30, i.e. in contact with the syringe piston. The plate 25 also supports a drip tray 34 mounted on the slide 28, for example, by means of a drive member 35 suitable fo causing it to pivot in a plane perpendicular to the plane of the slide 28 so that the tray moves between a rest position and a position in which it is situated immediately below the needle 31 of the syringe 30.

The carriage 20 has a second fixing plate 36 which is extended at its base by a horizontal bracket 37. The plates 36 and 25 are preferably disposed on opposite sides of the support and guide path 21 as shown in FIG. 1. However, a different structural disposition could alternatively be used.

The bracket 37 supports a moving module for temporary storage of the flasks 1, which module may essentially be constituted by a carrousel 38 associated with a drive member 39. The periphery of the carrousel 38 has a plurality of vertical axis slots 40 disposed at equal angles thereabout and each having a window 40a. The slots 40 are intended to contain respective flasks 1 filled with a sample of substance to be analysed and having an identifying code on the outside, for example a bar-type code. Each flask 1 is preferably encoded with three different items, namely: the substance contained; the analysis method to be used on said substance; and a processing priority number appropriate to the sample.

The motor 39 is suitable for rotating the carrousel 38 through steps corresponding to the angular pitch of the slots 40, and relative to an indexing position such that one of the slots 40 is always engaged in an extraction station 41, as shown in FIG. 1. The extraction station 41 includes a head 42 disposed vertically above the carrousel 38 and preferably fitted with two needles. The head 42 is associated with a motor 43 suitable for displacing it in a horizontal direction radially relative to the carrousel 38. The motor 43 is carried by a motor 44 capable of moving the head 42 vertically towards or away from a slot 40 stopped at the station 41. The motor 44 is preferably constituted by a double-acting actuator carried by the plate 36. One of the needles of the head 42 is in communication via a circuit 45 with a supply 46 of inert fluid under pressure. The other needle of the head 42 is in communication via a transfer circuit 47 with the syringe 30 of the injector head 26.

The bracket 37 also supports a tank 48 containing a cleaning liquid or solvent which is permanently connected to a dip pan 48a lying on the radial direction in which the motor 43 can drive the head 42.

The bracket 37 supports a reader 49 for reading the codes carried on the flasks 1. The reader 49, which is preferably of the laser type, is placed to look through the window 40a of one of the slots 40 whenever the carrousel 38 is in a stop position so as to be able to read the code of the flask 1 occupying said slot.

The above-described apparatus also includes the calculating machinery III which is programmed so as to determine, by means of detectors 50 and a corresponding number of dedicated circuits 51, the state of each of the analysis stations 9 (i.e. whether in operation or available) and the analysis characteristics of these stations are stored in a file module 52. On the basis of its detectors 50 and of the information in the file module 52, the machinery III is capable of permanently keeping track of which analysis stations are ready for use and what types of analysis they can perform.

The calculating machinery III also includes a module 53 for storing the information read by the reader 49 and transmitted over a link 49a. The module 53 takes account of the identification information on each sample, the information indicative of the analysis treatment to which the sample is to be subjected, and the information relating to the nature of the associated priority. These various items of information are stored in conjunction with an address code enabling the position of each flask 1 on the carrousel 38 to be determined relative to an origin position in which a given slot 40 is vertically under the extraction station 41. Such an address code can be provided in various different ways, either by incorporating an identity code in each slot, or else by a counting system which counts each time the carrousel 38 moves in a given direction from a starting position which the carrousel automatically takes up under the control of the motor 39.

Figure 3:
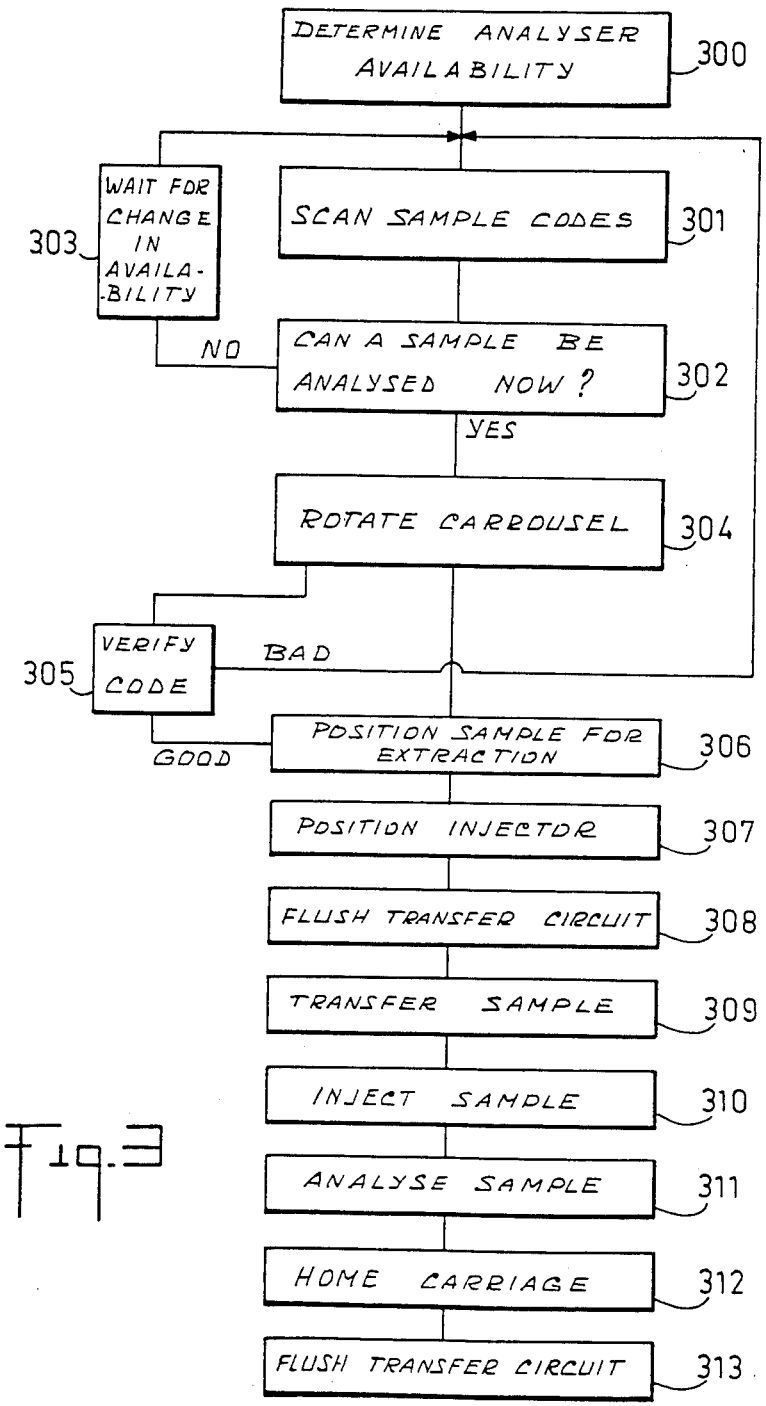
FIG. 3 is a simplified flowchart of the various successive steps implemented by the apparatus in operation.

FIG. 1 shows that the calculating machinery III is connected via dedicated links 54 to 60 to the drive members 39, 43, 44, 23, 29, 32, and 35 respectively in order to control the operation of these various members as a function of an operating cycle which is described in greaer detail below with reference to the flowchart of FIG. 3.

The operating cycle begins with a preliminary carrousel loading step in which at least some of the slots 40 have respective flasks 1 entered therein. The first operating step controlled by the calculating machinery III consists in analyzing the detectors 50 in order to store in the file 52 which station or stations 9 are available. This first step is referenced 300 in the flowchart and is followed by a step 301 which consists initially in powering the drive member 39 so as to rotate the carrousel 38 in a single direction of rotation away from an origin position in which a reference slot 40 is situated beneath the extraction station 41. This operating step is a scanning step and requires a full turn of the carrousel 38 so as to cause each of the slots 40 to move past the reader 49 one by one. Each of the codes read in the slots 40 is then stored in the module 53.

The calculating machinery III then, during step 302, uses a module 61 to compare the information relating to the specific treatments of the samples temporarily stored in the carrousel 38 with the characteristics of the available analysis station(s) 9, so as to establish a temporary correspondence table in which the samples are sorted by priority order. This search for an available analyzer may provide an entirely negative result in the event that regardless of the priority rating of the samples, none of them is suitable for being processed by any of the presently available analyzer stations. In such an event, the calculating machinery III stores the information supplied by the reader 49 during a step 303 while waiting for the detectors 50 to indicate a change in the availability status of the stations 9 as stored in the file 52. When such a change in availability takes place, the calculating machinery III repeats the above-described steps 301 and 302.

In the contrary case, the calculating machinery III determines which is the highest priority sample for which there is at least one analysis station 9 available for performing the analysis required by the sample, and then controls the motor 39 to rotate the carrousel 38 as a function of the address of the slot 40 which is occupied by the flask 1 containing highest priority sample to be analyzed. The motor 39 rotates the carrousel during step 304 until the appropriate slot is placed beneath the extraction station 41.

In a variant method, as illustrated by step 305, the carrousel 38 is rotated by the motor 39 so as to bring the selected slot 40 in front of the reader 49 in order to reread the bar-code on the flask 1 so as to validate the choice which has been made and avoid any risk of error which could arise if the flask contained in the slot has been changed, either deliberately or by accident. If the validation test fails, then the calculating machinery returns to the sample code scanning step 301 as described above.

If the validation check is good, the calculting machinery III operates the drive member 39 to rotate the carrousel 38 in order to bring the appropriate slot 40 and the flask 1 containing the sample to be processed into the reference position relative to the extraction station 41. This positioning step 306 is followed by a step 307 during which the calculating machinery 111 powers the motor 23 so as to move the carriage 20 along the support and guide path 21 in order to bring the injection head 26 over the injector 12 of the available station 9 whose analysis characteristics are appropriate for the processing to be applied to the selected sample.

In the next step 308, the calculating machinery III controls the motor 43 so as to move the head 42 over the dip pan 48a and the machinery III then powers the motor 44 so as to move the head 42 relative to said dip pan. The machinery III then controls the motor 35 to bring the drip tray 34 beneath the needle 31 of the syringe 30. In the next step, the machinery III temporarily opens the tank 46 to admit a fraction of the flushing liquid contained in the tank 48 via the head 42 and to cause this liquid to pass along the circuit 47, the syringe 30 and the needle 31. Step 308 terminates with the head 42 returning to its original rest position where it is over the flask 1 containing the product to be analyzed and with the drip tray 34 being returned to its retracted position.

In the next step, 309, the calculating machinery III powers the motor 44 to lower the head 42 and cause its needles to pass through the septum which hermetically closes the flask 1. The tank 46 is then opened again in order to cause a predetermined quantity of sample to be taken from the flask 1 and to pass via the circuit 47 into the syringe 30.

The calculating machinery III then controls the motor 29 to lower the syringe 30 and cause its needle 31 to penetrate into the injector 12. This operating step 310 further includes the motor 32 being powered to displaced the piston 33 of the syringe 30 in order to inject the extracted quantity of sample into the injector 12 whose operation is controlled by a dedicated control line 63 by the calculating machinery III, as is the operation of the station 9.

The injected sample is analyzed at step 311 by means of a qualitative and a quantitative analysis process, in the present case by chromatography, with the duration of said process being transmitted to the calculating machinery III by means of the corresponding detector 50. During a step 312, the machinery III reverses the drive member 29 in order to disengage the injection head 26 from the injector 12. During a subsequent portion of this step, the machinery III powers the motor 23 to move the carriage 20 in translation and return it to its original waiting or "home" position.

The final step 313 consists in flushing the transfer circuit a second time in the manner described above at step 308.

The calculating machinery III is then ready to control a new operating cycle, as described above.

In a variant of the method, instead of flusing the system for extracting, transferring and injecting the sample during step 302 with a flushing fluid, it may be flushed with a first quantity of the sample substance which is evacuated via the drip tray 34. In this case, only the second flushing step 313 which takes place after injection is performed as described above with reference to step 308 by taking a flushing liquid from the pan 49.

As can be seen from the above-described method, the invention makes it possible to take account of the availability of one or more analysis stations in a battery of such stations capable of performing different types of analyses, to seek information relating to samples in a collection of samples to be processed, said information relating not only to the identity of each sample but also to the specific treatment to be applied to each of them and to a treatment priority order, thereby making it possible by performing comparisons with two continuously updated lists to determine which is the most urgent analysis that can be performed given analysis equipment availability, and then to ensure that said sample analysis is the next to be performed via an available and compatible analysis station regardless of the order in which sample flasks arrive and/or are stored in a temporary storage module.

It thus becomes possible to use a large capacity analysis and inspection installation for remote control of various different industrial processes taking place simultaneously on the basis of samples specific to each of them and arriving in a completely random manner at the analysis installation.

Various additional features may be provided to the above-described apparatus. For example, the carrousel 38 may have means fitted thereto for rotating each flask 1 when stopped in front of the reader 49 so as to improve the readability of its bar-codes.

An ejector device may be fitted to the bracket 37 in order to automatically remove each empty or partially emptied flask 1 after the corresponding sample has been fully analyzed. Flask-receiving containers may be provided in association with each analysis station 9 on the structure 22 for receiving the removed flasks to enable the number of samples treated thereby to be subsequently counted.

FIG. 1 also shows that the treatment assembly may be provided with a gutter 64 for collecting the flushing liquid or flushing sample portions which are ejected into the drip tray 34.

The invention is not limited to the example described above and shown in the drawings since numerous modifications may be made thereto without going beyond the scope of the claims. For example, the apparatus could be organized to operate by performing more than one injection from the substance contained in a single flask, in which case the flask capacity must be suitably large. Although the carriage 20 and the carrousel 38 are described above as being returned to their respective reference or home positions between two sample transfer operations, the person skilled in the art will readily understand that this is not essential and that the calculating machinery can keep track of their successive positions without homing them between operations.

I claim:

1. Apparatus for automatically taking and analyzing samples of substances made available in random manner, the apparatus being of the type comprising an analysis assembly including at least two analysis stations having different characteristics, and a module delimiting temporary storage slots for receptacles containing different substances to be analyzed by different methods applicable to each of said substances, said apparatus comprising:

receptacles each bearing a code identifying the substance contained therein, the analysis treatment to which it is to be subjected, and a treatment priority attributed thereto;

means for detecting the in-use or available status of each analysis station;

means defining slots each bearing a code corresponding to an address;

means for scanning the slots in the storage module for reading the codes of the slots and the code of the receptacles stored in the slots and for storing said codes in priority order in conjunction with the characteristics of the corresponding treatment and the addresses of the slots;

means for seeking in priority order correspondence between a treatment to be performed and a currently available compatible analysis station and for selecting the sample receptacle bearing such a treatment;

means for displacing an insertion system from an original position into relationship with the available analysis station;

means for bringing the selected sample receptacle into relationship with an extraction station;

means for extracting at least a portion of the sample from the selected receptacle and for transferring it into the insertion system;

means for inserting the sample into the analysis station;

means for controlling the operating conditions of the analysis station as a function of the analysis treatment to be performed; and means for returning the insertion system to its original position in readiness for a new operating cycle.

2. Apparatus according to claim 1, including means for flushing the insertion system with the substance to be analyzed prior to inserting at least a portion of the sample into the analysis station, and for flushing the insertion system with a flushing liquid after said portion sample has been inserted and said insertion system has been returned to its original position.

3. Apparatus according to claim 1, including means suitable for re-reading the information on the various different receptacles prior to extracting substance therefrom.

4. Apparatus according to claim 1, including means suitable for ejecting said receptacle from the storage module prior to returning said storage module to its original position.

5. Apparatus for automatically taking and analyzing samples of substances made available in random manner, the apparatus being the type comprising an analysis assembly, an assembly for temporarily storing and transferring same receptacles, and means suitable for extracting at least a portion of the sample from a receptacle in order to insert it into the analysis assembly, the apparatus comprising:

an analysis assembly constituted by at least two analysis stations having different characteristics and associated with detectors for detecting their respective in-use or available statuses; 'a storage assembly for temporarily storing and for transferring samples, said assembly being suitable for being displaced and halted in relationship with the analysis stations and itself comprising:

a moving module for temporary storage delimiting slots coded with address information for receiving receptacles containing samples of substance to be analyzed, each receptacle carrying at least a code identifying the substance contained therein, a code identifying the analysis treatment to be performed, and a code giving the priority of the associated treatment;

an extraction system for extracting a sample from any of said receptacles;

an insertion head in communication with the extraction system and compatible with each of the analysis stations; and a code reader for reading each receptacle in relationship with the position it occupies in the storage module; and calculating machinery controlling the operating cycle of the storage assembly and of the analysis assembly each time that a correspondence occurs between the code of a receptacle read by the reader and the available status of a compatible analysis station as provided by its detector.

6. Apparatus according to claim 5, wherein the assembly for temporary storage and transfer of samples includes a support and guide path extending parallel to a line of analysis stations and detector means, and on which path a motor-driven carriage is mounted supporting the moving storage module, the extraction system, the insertion head, and the code reader.

7. Apparatus according to claim 6, wherein the assembly for temporary storage and transfer comprises:

a side-mounted bracket on said carriage;

a rotary carrousel delimiting open slots for temporary storage of the receptacles, which receptacles bear at least one code readable through an opening in the slots;

a carrousel drive motor for driving the carrousel from an indexing position thereof;

a motor-driven extraction system occupying and indexing position;

a tank of flushing liquid associated with means for connection with the extraction system; and a code reader situated facing a slot in the indexing position of the carrousel.

8. Apparatus according to claim 7, wherein the carrousel includes means for rotating the receptacles about their axes when the receptacles are in their respective slots.

9. Apparatus according to claim 8, wherein the carrousel includes means for ejecting receptacles after the samples contained therein have been analyzed.

10. Apparatus according to claim 5 or 6, wherein the assembly for temporary storage and for transfer comprises a plate supporting a motor-driven insertion head which is connected to the extraction system, and a drip tray for recovering and removing the flushing liquids.

* * * * *